(12) United States Patent
Pace

(10) Patent No.: US 11,583,229 B2
(45) Date of Patent: Feb. 21, 2023

(54) NON-RIGID WEARABLE DEVICES

(71) Applicant: ABBOTT DIABETES CARE INC., Alameda, CA (US)

(72) Inventor: Louis G. Pace, San Carlos, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 509 days.

(21) Appl. No.: 16/705,956

(22) Filed: Dec. 6, 2019

(65) Prior Publication Data

US 2020/0222003 A1 Jul. 16, 2020

Related U.S. Application Data

(63) Continuation of application No. 15/154,272, filed on May 13, 2016, now Pat. No. 10,531,831.

(60) Provisional application No. 62/161,721, filed on May 14, 2015.

(51) Int. Cl.
*A61B 5/00* (2006.01)
*A61B 5/145* (2006.01)

(52) U.S. Cl.
CPC ............ *A61B 5/6833* (2013.01); *A61B 5/002* (2013.01); *A61B 5/14532* (2013.01); *A61B 2562/164* (2013.01); *A61B 2562/166* (2013.01)

(58) Field of Classification Search
None
See application file for complete search history.

(56) References Cited

U.S. PATENT DOCUMENTS

| | | |
|---|---|---|
| 2013/0150691 A1 | 6/2013 | Pace et al. |
| 2015/0018643 A1 | 1/2015 | Cole |
| 2016/0120433 A1 | 5/2016 | Hughes et al. |

*Primary Examiner* — Jay B Shah
(74) *Attorney, Agent, or Firm* — One LLP

(57) ABSTRACT

Systems, devices, and methods are provided for a non-rigid wearable device comprising electrical circuitry and a support structure supporting the electrical circuitry. The support structure having rigid sections that rigidly support components of the electrical circuitry to protect components and/or solder joints from stress due to deflection and having non-rigid or flexible sections where there are no solder connections present on the electrical circuitry and/or where there are interconnecting traces present on the electrical circuitry that can tolerate stress due to deflection.

16 Claims, 6 Drawing Sheets

NON-RIGID WEARABLE DEVICES

CROSS-REFERENCE TO RELATED APPLICATIONS

This application is a continuation of U.S. application Ser. No. 15/154,272, filed May 13, 2016, which claims priority to and the benefit of U.S. Provisional Application Ser. No. 62/161,721, filed May 14, 2015, both of which are incorporated by reference herein in its entirety for all purposes.

FIELD

The subject matter described herein relates generally to wearable devices, for example, within an analyte monitoring environment.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost. For these and other reasons, needs exist for improved analyte monitoring systems, devices, and methods.

SUMMARY

A number of systems have been developed for the automatic monitoring of the analyte(s), like glucose, in a bodily fluid of a user, such as in the blood, interstitial fluid ("ISF"), dermal fluid, or in other biological fluid. Some of these systems include a sensor that can be at least partially positioned "in vivo" within the user, e.g., transcutaneously, subcutaneously, or dermally, to make contact with the user's bodily fluid and sense the analyte levels contained therein.

As such, these systems can be referred to as "in vivo" monitoring systems. In vivo analyte monitoring systems include "Continuous Analyte Monitoring" systems (or "Continuous Glucose Monitoring" systems) that can broadcast data from a sensor control device to a reader device continuously without prompting, e.g., automatically according to a broadcast schedule. In vivo analyte monitoring systems also include "Flash Analyte Monitoring" systems (or "Flash Glucose Monitoring" systems or simply "Flash" systems) that can transfer data from a sensor control device in response to a scan or request for data by a reader device, such as with an Near Field Communication (NFC) or Radio Frequency Identification (RFID) protocol. In vivo analyte monitoring systems can also operate without the need for finger stick calibration.

The in vivo analyte monitoring systems can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level. While in many of the present embodiments the monitoring is accomplished in vivo, the embodiments disclosed herein can be used with in vivo analyte monitoring systems that incorporate in vitro capability, as well has purely in vitro or ex vivo analyte monitoring systems.

The sensor is generally part of a sensor control device that resides on (or in) the body of the user and contains the electronics and power source that enable and control the analyte sensing. The sensor control device, and variations thereof, can be referred to as a "sensor control unit," an "on-body electronics" device or unit, an "on-body" device or unit, or a "sensor data communication" device or unit, to name a few.

The analyte data sensed with the sensor control device can be communicated to a separate device that can process and/or display that sensed analyte data to the user in any number of forms. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. The reader device can be a dedicated use device, a smart phone, a tablet, a wearable electronic device such as a smart glass device, or others.

Provided herein are a number of example embodiments of systems, devices, and methods directed to or including a non-rigid or flexible wearable device. For ease of illustration, this wearable device will be described as a sensor control device for use in an in vivo analyte monitoring system. However, in its broadest sense, the wearable device can be any type of device, wearable on any portion of the body, for which added flexibility is desired, and can be a medical device for use in a medical environment or can be a non-medical device for use in environments other than medical ones.

In certain embodiments, a wearable device that attaches to the skin of a user is provided. The attachment can be made by an adhesive disposed on a skin-contacting surface of the device 10 or in another manner such as with a mechanical connector like a belt or strap, which can be used in addition to or instead of adhesive. The device includes a cover, electrical circuitry (i.e., one or more electrical circuits) with rigid and flexible electrical components for collecting data, storing data, processing data, transmitting data, or performing passive electrical functions (e.g., loading, biasing, switching, matching, etc.), a support structure for supporting the electrical circuitry, and an adhesive patch coupled to the support structure. The support structure includes rigid or substantially rigid sections where components that are soldered to pads on the electrical circuitry are rigidly supported and flexible sections where no solder connections are present on the electrical circuit. The rigid or substantially rigid sections of the support structure are configured beneath the rigid components of the electrical circuitry to protect solder joints from stress due to deflection. The non-rigid, substantially non-rigid, or flexible sections of the support structure are configured beneath areas where no solder connections are present on the electrical circuit and/or where interconnecting traces are present that can tolerate stress due to deflection. The flexible sections allow the device to conform to a user's skin surface contour and accommodate movement of the user's skin, thereby improving adhesion to the body and comfort over the wear duration.

Some example embodiments of the methods include providing a rigid or substantially rigid material and removing sections of the rigid material to create a geometric pattern of rigid sections in spaced relation with and without interlocking features extending there between. The geometric pattern may define the flex of the support structure.

The flexible sections or elements defined in the rigid material may function (or be configured) as a living hinge or mechanical hinge and allow the support structure to bend or flex. In some embodiments, the flexible sections may be positioned at substantially any location of the rigid material and may span across one or more dimensions of the rigid material (e.g., across a width, length, or height of the rigid material).

In other embodiments, the device includes a sensor element and socket capable of coupling to the electrical circuit.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

The present subject matter is not limited to the particular embodiments described, as those are only examples and may, of course, vary. Likewise, the terminology used herein is for the purpose of describing particular embodiments only, and is not intended to be limiting, since the scope of the present disclosure will be limited only by the appended claims.

In many example embodiments, a wearable device 10 that attaches to the skin of a user is provided. The attachment can be made by an adhesive disposed on a skin-contacting surface of the device 10 or in another manner such as with a mechanical connector like a belt or strap, which can be used in addition to or instead of adhesive.

Figure 1:
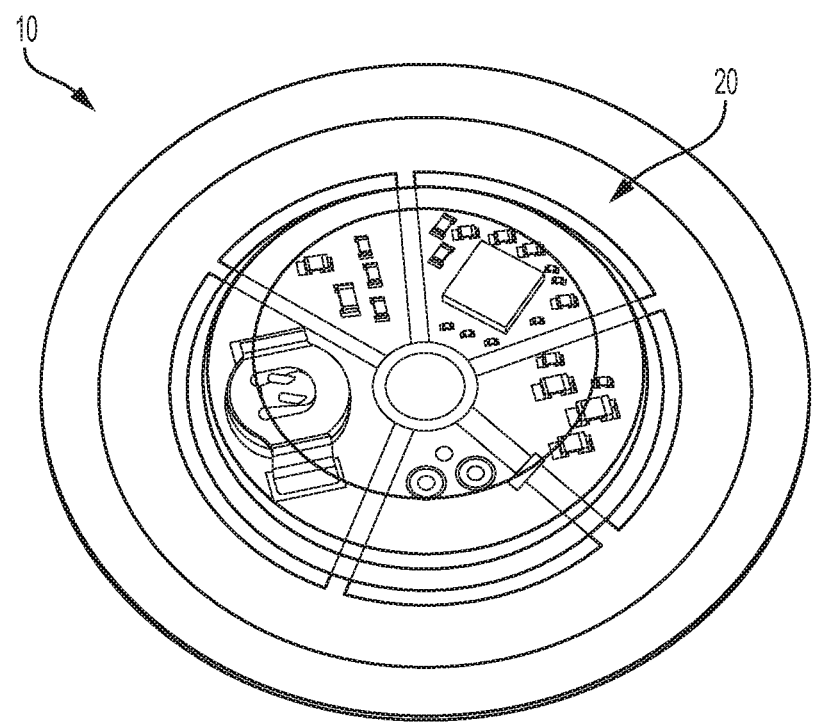
FIG. 1 is a top perspective view of an assembled non-rigid wearable device.
Figure 2:
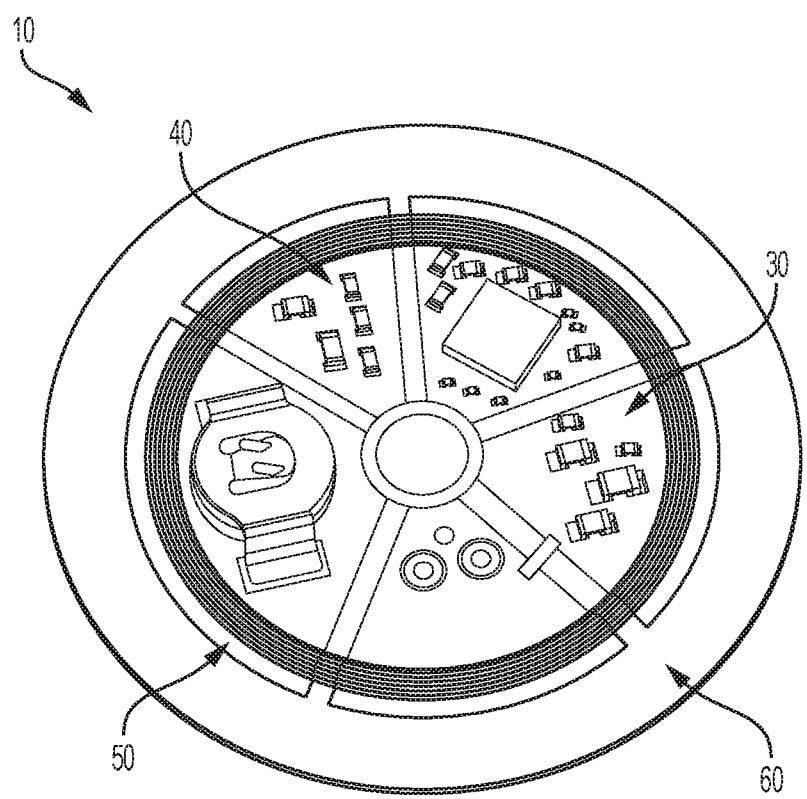
FIG. 2 is a top perspective view of a partially assembled non-rigid wearable device of FIG. 1 with its cover removed.
Figure 3:
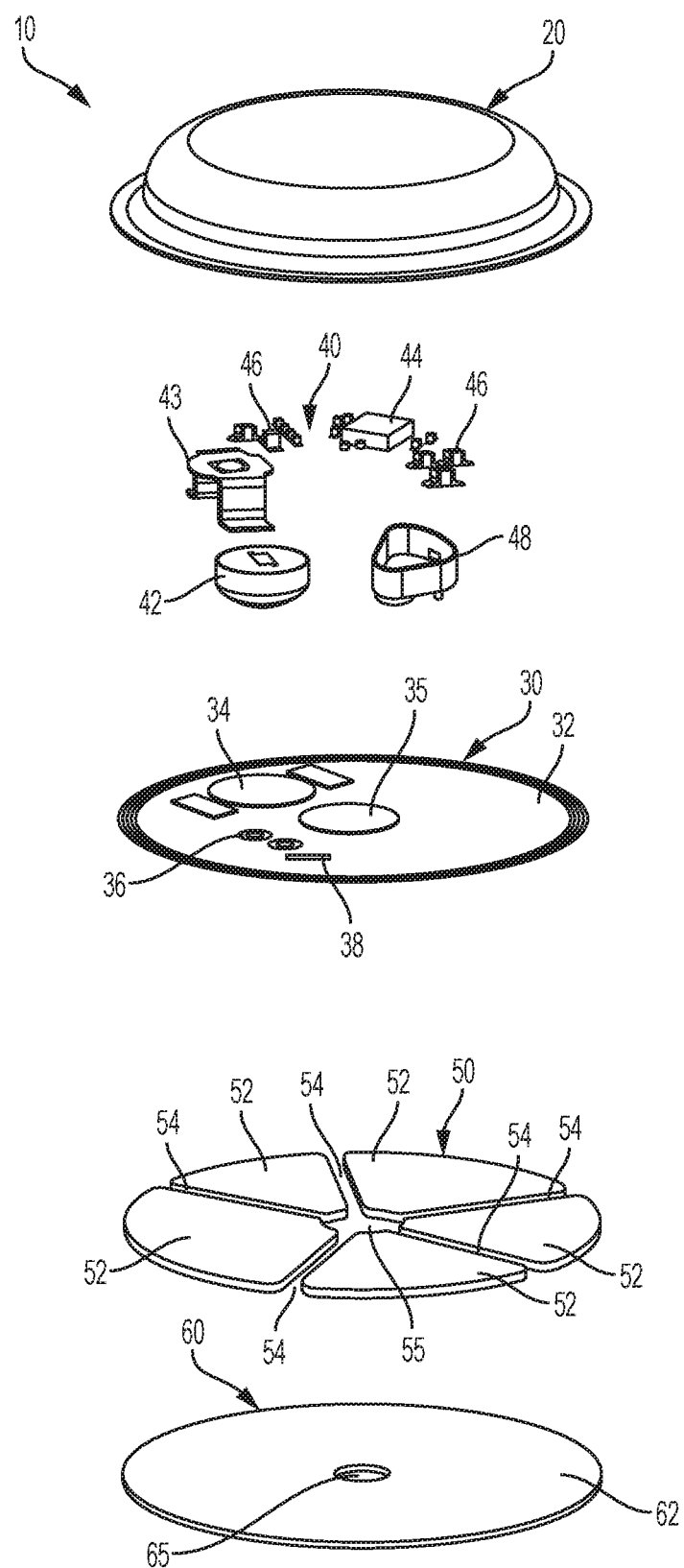
FIG. 3 is a perspective exploded assembly view of the non-rigid wearable device of FIG. 1.

Turning to FIGS. 1, 2 and 3, the device 10 is depicted as including an upper housing (e.g., a cover or seal) 20, electrical circuitry comprising a flexible electrical circuit board 30 along with electrical components 40 coupled thereto for collecting data, storing data, processing data, transmitting data, or performing passive electrical functions, an optional support structure 50 for supporting the circuit board 30, and an adhesive patch 60 coupled to the support structure 50 and configured to adhere the device 10 to the skin of a user.

The construction of the wearable device 10 described with respect to the following FIGS. 1-7B is similar to those described in U.S. Publication No. 2013-0150691 ("Analyte Sensor Devices, Connections, and Methods") and U.S. Publication No. 2015-0018643 ("Systems, Devices, and Methods for Energy Efficient Electrical Device Activation"), both of which are incorporated by reference herein in their entirety and for all purposes. In the present description, the wearable device 10 is described with features that facilitate the device conforming to a user's skin, adhesion to the body and comfort over the wear duration.

Turning to FIG. 3, the circuit board 30 is shown to include a conductive trace 32 about its periphery that may function as an antenna, battery contacts 34, sensor contacts 36, an interior conductive trace 38 that enables communication between rigid components 40 adhered to the circuit board 30, etc. The rigid components 40 include a battery 42, a battery mount 43, a processor 44 (e.g., an ASIC including a communications facility) along with one or more other associated components 46 (e.g., discrete components such as resistors, inductors, capacitors, transistors, chips, and so forth). Rigid components 40 can be components that are themselves rigid. Rigid components 40 can also be components that are not themselves rigid but, regardless, it is desirable to keep those components in a rigid state. For example, such components could be sensitive to the mechanical stress that accompanies bending of the underlying substrate (or susceptible to fatigue failure from such mechanical stress), either due to the component's fragile structure itself or the fragile connections of the component to the substrate (e.g., a fragile adhesive bond or solder connection). The components 40 are shown coupled or secured (e.g., adhered with adhesive or solder) to the circuit board 30 in FIGS. 2 and 4. Where the wearable device 10 is a sensor control device, a sensor socket 48 configured to receive a sensor and other associated components (not shown) is provided.

As shown in FIGS. 2, 3, 4 and 5a-5b, the support structure 50 includes rigid or substantially rigid sections 52 in spaced relation with one another forming gaps or channels 54 between adjacent sections 52. When assembled with the circuit board 30, the rigid or substantially rigid sections 52 of the support structure 50 are configured or oriented beneath the rigid components 40 of the electrical circuit to, e.g., protect solder joints from stress due to deflection. The gaps or channels 54 form non-rigid or flexible sections of the support structure 50 that are configured or oriented beneath areas of the circuit board 30 where no solder connections are present on the electrical circuit and/or where interconnecting traces that can tolerate stress due to deflection, such as, e.g., the interior traces 38 and peripheral traces 32, are located.

In a broad sense, circuitry can be provided on one or more first portions (e.g., sections 52) and added flexibility for improved wearability can be provided by one or more second portions (e.g., gaps 54), where the first portion can be described as relatively more rigid than the second portion, or where the first portion can be described as relatively less flexible than the second portion, and so forth. Put differently, the first portion can be described as rigid, substantially rigid, non-flexible, or substantially non-flexible and the second portion can be described as flexible, substantially flexible, non-rigid, or substantially non-rigid. Those of ordinary skill in the art will readily understand the concepts of rigidity and flexibility and will understand the meaning of these terms as they are used herein to provide a wearable device, without need for a definition based on explicit numerical ranges, ASTM (American Society for Testing and Materials) standards, etc.

In this and all embodiments, any number of rigid or substantially rigid sections 52 can be present, and any number of non-rigid or flexible sections can be present. The width of a particular flexible section or gap can be constant or variable, and the width of flexible sections or gaps within the same device can be the same or different from each other.

Any number of interior traces 38 and/or peripheral traces 32 can be included to connect components on the different rigid sections 52. Each trace 32 and 38 can extend from one rigid section 54 to only the immediately adjacent rigid section 54 (on either side), or can bridge one or more rigid sections 54 such that a component 40 on one rigid section 54 is directly electrically connected with a component 40 on another, non-adjacent rigid section 54. Although the term "trace" is used herein, in all embodiments any element capable of transferring a signal can be used, including but not limited to a conductive wire, either with or without an insulating jacket, a conductive ribbon cable, a waveguide, and the like.

It should be noted that the term "rigid material" as used herein is meant to encompass rigid materials, semi-rigid (partially flexible materials), and substantially any materials where an increased rigidity may be desired. For example, the rigid material may be metal, carbon fiber, ceramics, glass, sapphire, plastic, composite materials (e.g., carbon fiber reinforced plastic, glass fiber reinforced materials, or the like), printed circuit boards, and the like. Further, the dimensions of a material, such as its thickness, may be adjusted to cause that material to be relatively more rigid or less rigid (or more flexible, etc.) when compared to the same material at a different dimension, and thus certain materials may be considered either rigid or non-rigid depending on its dimensions. Additionally, the rigid material may include a combination of two or more materials connected together (e.g., through adhesive, welding, or the like). As one example, in instances where a first material may be brittle (e.g., glass), the material may be laminated or otherwise connected to another less brittle material and then the combined material may be modified using the method.

The support structure 50 may be formed by providing a rigid or substantially rigid material and removing sections of the rigid material to create a geometric pattern of rigid sections 52 in spaced relation with or without interlocking features extending there between. The geometric pattern may define the flex of the support structure 50.

Figure 5A:
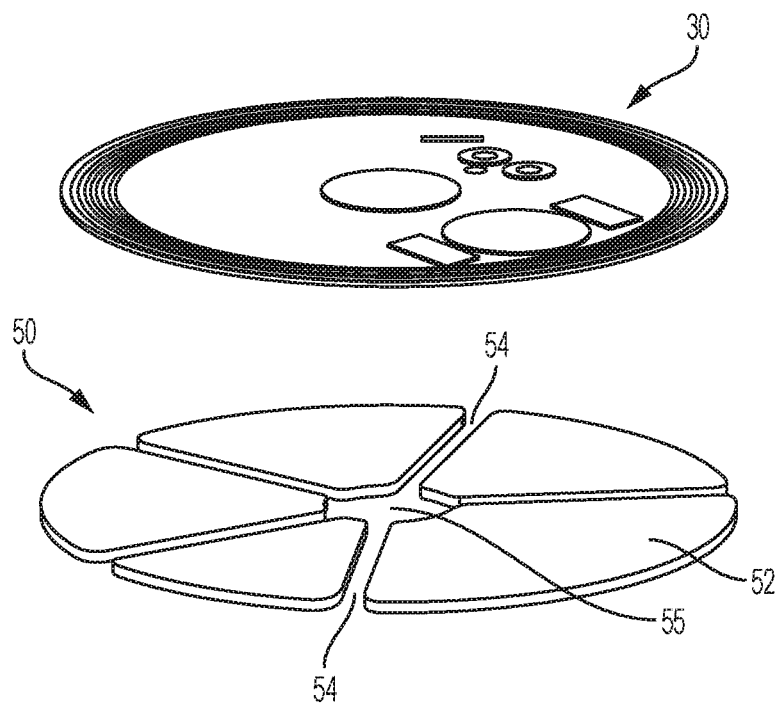
FIGS. 5a and 5b are perspective exploded assembly views of the circuit board and alternate embodiments of the support structure.

As depicted in FIG. 5a, an example support structure 50 is circular in shape with the individual rigid sections 52 being formed as individual truncated pie-shaped sections defining an opening 55 at the center of the support structure 50. The gaps or channels 54 between adjacent rigid sections 52, which form the flexible sections of the support structure 50 when adhered to the circuit board 30 and adhesive patch 60, radially extend from the central opening 55 to the outer periphery of the support structure 50.

Figure 5B:
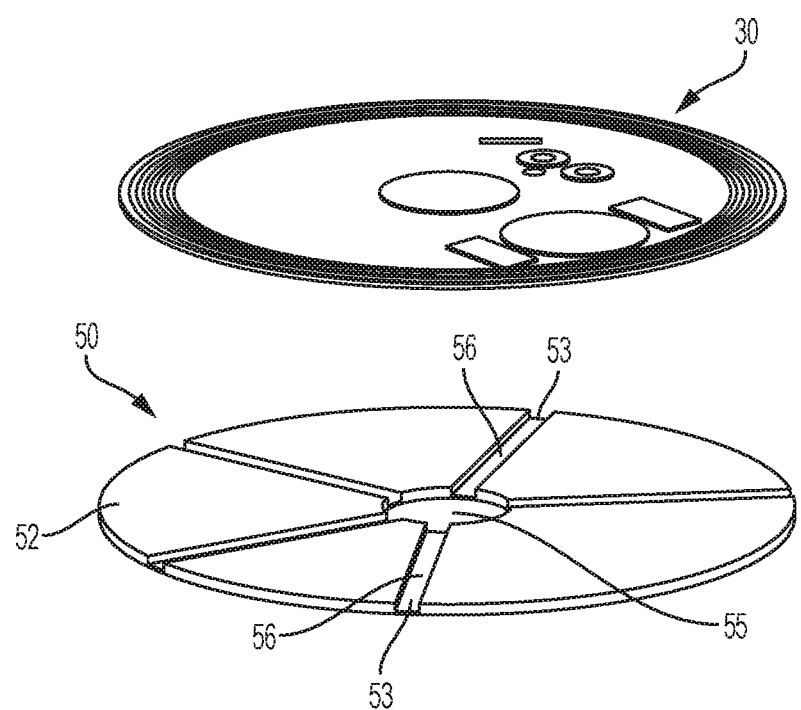

Alternatively, as shown in FIG. 5b, the flexible sections or elements defined in the rigid material may function as a living hinge or mechanical hinge and allow the support structure 50 to bend or flex. Instead of removing all material or there being no material between adjacent rigid sections 52, the flexible sections or elements comprise a groove or 3-sided channel 56 with a wall section 53 of the same material extending between adjacent rigid sections 52, where the material of wall section 53 is relatively thinner than the adjacent rigid sections 52. The thin wall sections 53 each function as a living hinge allowing the support structure 50 to bend or flex.

In other embodiments, one or more living hinges (or mechanical hinges) can be present along with one or more gaps between two adjacent rigid sections, resulting in a combination of the approaches shown in FIGS. 5a and 5b. Such a configuration can provide increased flexibility (by virtue of the gap(s)) and also maintain a constant or substantially constant spacing between rigid sections (by virtue of the living hinge(s)) so as to, e.g., avoid placing too great of a load on the traces 32 and/or 38 extending between the two adjacent rigid sections.

Figure 6A:
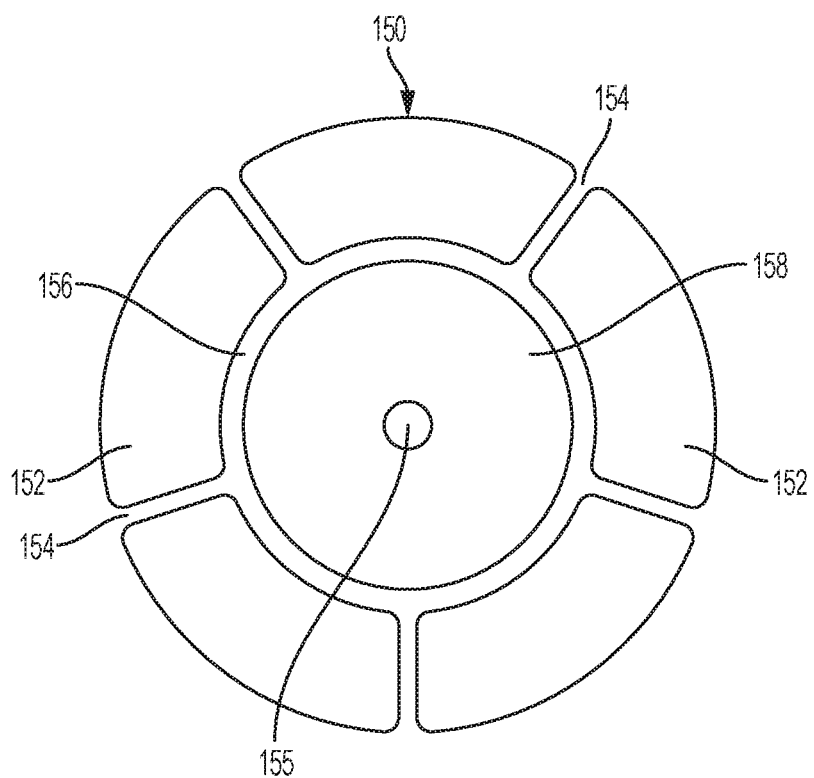
FIGS. 6a and 6b are top views of alternate embodiments of the support structure.
Figure 6B:
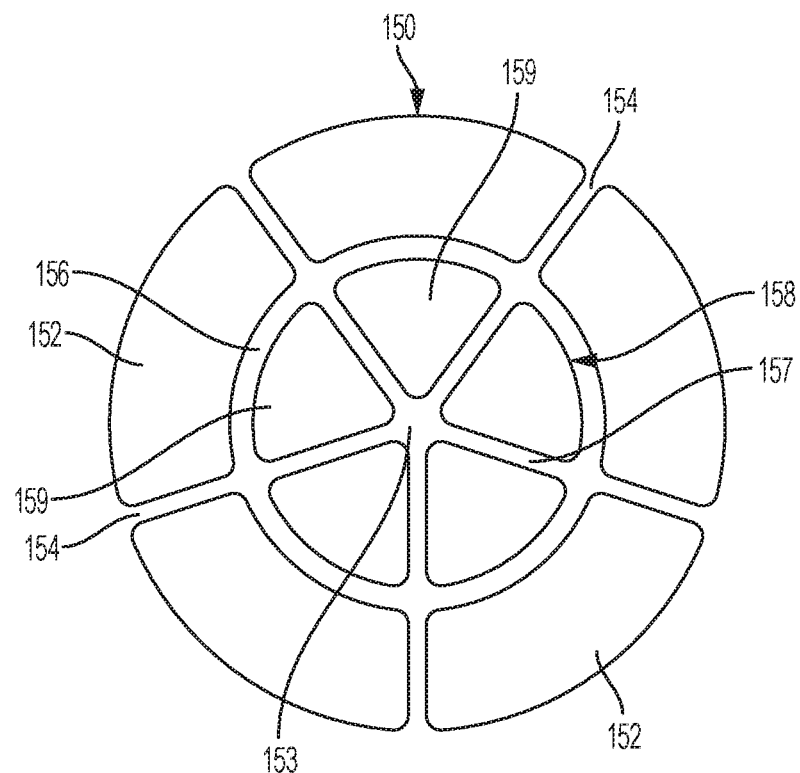

The flexible sections may be positioned at substantially any location of the rigid material and may span across one or more dimensions of the rigid material (e.g., across a width, length, or height of the rigid material) forming a variety of geometric patterns. Turning to FIGS. 6a and 6b, two example alternative embodiments of a support structure 150 with rigid and flexible sections are shown. In FIG. 6a, the support structure 150 includes truncated pie shape rigid sections 152 (which can also be described as curved elongate shapes) positioned about a central rigid section 158, which is circular in shape with a central opening 155 formed there through. In this and all embodiments, the rigid sections 12 can have rounded corners (as shown here) or sharp corners. The rigid sections 152 are positioned in spaced relation with the central rigid section 158 with a circular gap or channel 156 formed there between and extending about the periphery of the central rigid section 158. Adjacent rigid sections 152 are positioned in spaced relation with one another with gaps or channels 154 radially extending from the circular gap 156 to the outer periphery of the support structure 150.

In an alternative, as shown in FIG. 6b, the central rigid section 158 may comprise individual, truncated pie shaped central rigid sections 159 defining a central opening 153. Adjacent rigid sections 159 are positioned in spaced relation with one another with gaps or channels 157 radially extending from the central opening 155 to the circular gap 156.

Figure 7A:
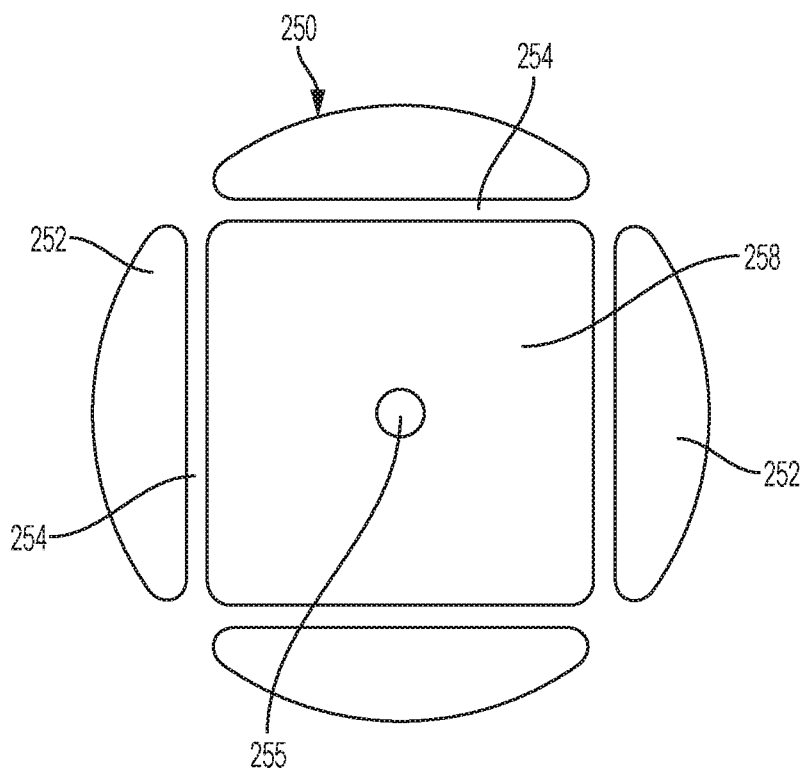
FIGS. 7a and 7b are top views of alternate embodiments of the support structure.
Figure 7B:
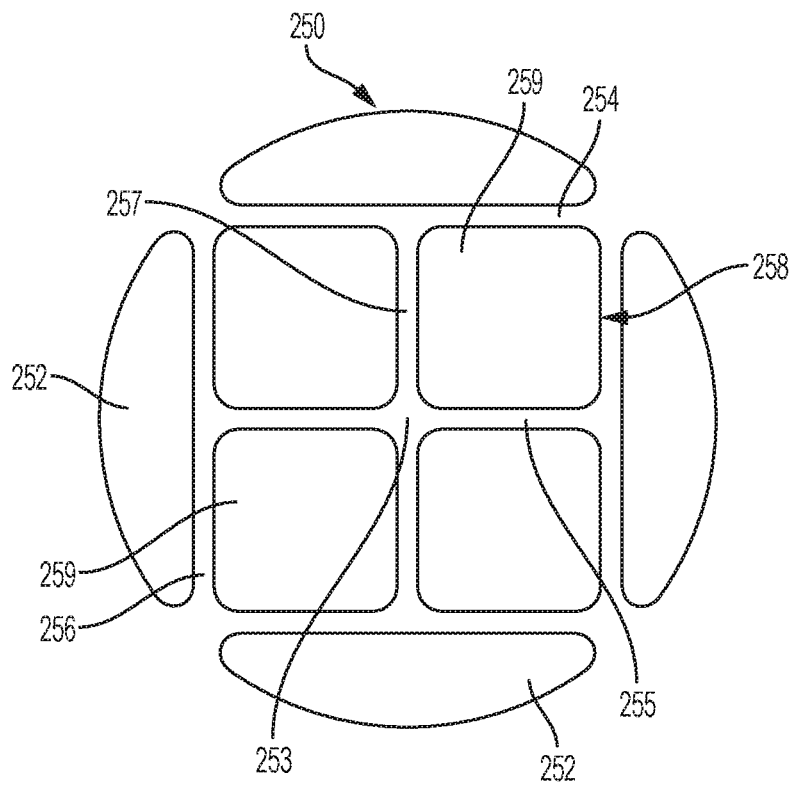

Turning to FIGS. 7a and 7b, two other example alternative embodiments of a support structure 250 with rigid and flexible sections are shown. In FIG. 7a, the support structure 250 includes truncated pie shape rigid sections 252 positioned about a central rigid section 258, which is square in shape with a central opening 255 formed there through. The rigid sections 252 are positioned in spaced relation with the central rigid section 258 and one another with a laterally and longitudinally oriented gaps or channels 254 and 256 formed there between and extending about the periphery of the central rigid section 258.

In an alternative, as shown in FIG. 7b, the central rigid section 258 may comprise individual central rigid sections 259 defining a central opening 153. The central rigid sections 259 are square in shape and positioned in spaced relation with one another with laterally and longitudinally oriented gaps or channels 255 and 257 extending through the central opening 253 and between the laterally and longitudinally oriented gaps or channels 254 and 256 extending about the periphery of the central rigid section 258.

Figure 8:
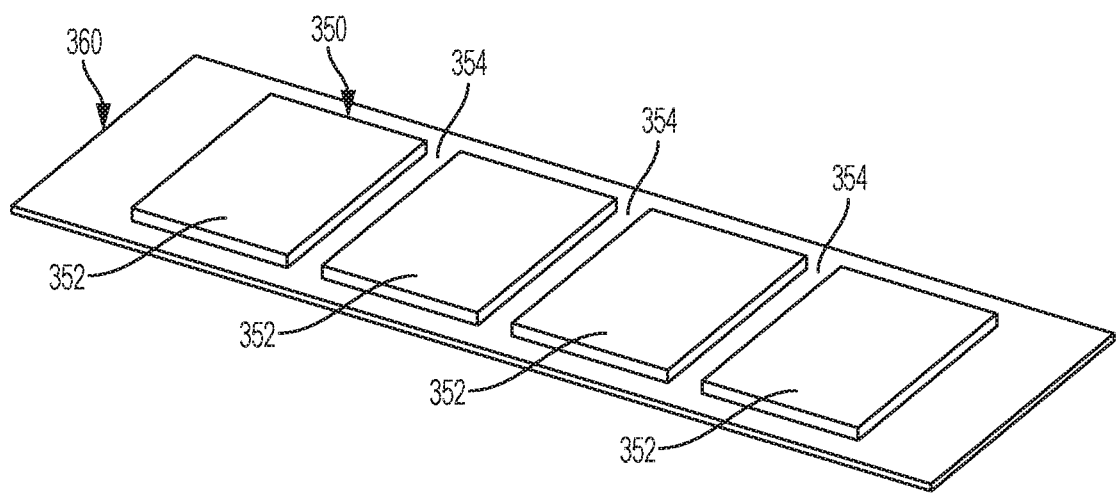
FIG. 8 is a perspective view of an alternate embodiment of the support structure and an adhesive patch assembled together.

Turning to FIG. 8, another example alternative embodiment of a support structure 350 with rigid and flexible sections are shown. The support structure 350 includes a series of rigid sections 352, which are square or rectangular in shape and linearly aligned and mounted on an adhesive patch 360. Individual rigid sections 352 are positioned in spaced relation with one another with gaps or channels 254 formed there between.

Figure 4:
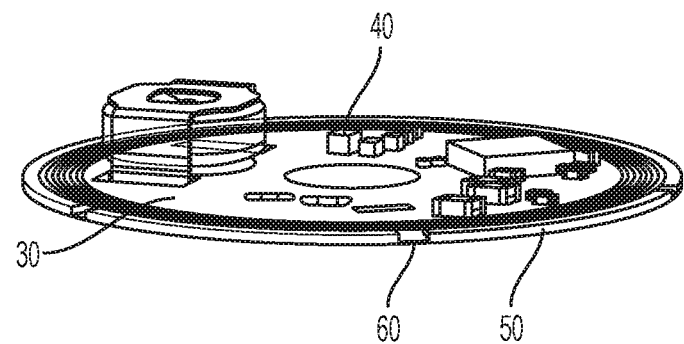
FIG. 4 is a perspective view of a populated circuit board, a support structure and an adhesive patch assembled together.

Turning back to FIGS. 2, 3 and 4, the adhesive patch 60 includes a body 62 with a central opening 65 there through. When assembled, as depicted in FIGS. 2 and 4, the central openings 35, 55 and 65 of the circuit board 30, support structure 55 and patch 65, respectively, align with one another to define a central opening through which an element, such as a sensor element (not shown) may extend. This overall sensor opening need not be located in the direct center of the device, and can be located in a position offset from center as well.

As noted above, the electrical circuit includes a peripheral trace 32 that may function as an antenna. Where the trace 32 functions as an antenna, the wearable device 10 is capable of communicating with another device, such as a reader device, utilizing transmissions over a wireless communication protocol including, but not limited to, a near field communication (NFC) protocol, an RFID protocol, a Bluetooth or Bluetooth Low Energy (BTLE, BLE, Bluetooth Smart, Bluetooth Smart Ready, a Wi-Fi protocol, a proprietary protocol, or the like.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a", "an", and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A wearable device wearable on a body of a user, comprising:
    a flexible circuit board comprising a plurality of conductive traces and a plurality of electrical components;
    a support structure coupled to the circuit board, the support structure comprising a plurality of first sections and at least one second section, wherein the plurality of first sections includes first and second first sections and the at least one second section includes a first second section, wherein the first second section is located in between and adjacent to the first first section and the second first section, wherein the support structure is bendable along the at least one second section, wherein the first first section and the second first section are in a single plane, and
    a flexible patch having a first surface and a second surface, wherein each of the plurality of first sections contacts the first surface of the flexible patch, and wherein the second surface is adhesive.

2. The device of claim 1, wherein the plurality of first sections further includes a third first section and the at least one second section further includes a second second section, and wherein the second second section is located in between and adjacent to the second first section and the third first section.

3. The device of claim 1, wherein one or more of the plurality of electrical components are coupled to one or more sections of the plurality of first sections.

4. The device of claim 1, wherein the at least one second section is positioned under the flexible circuit board absent electrical components coupled thereto.

5. The device of claim 1, wherein the at least one second section is positioned under an area of the flexible circuit board comprising one or more conductive traces of the plurality of conductive traces.

6. The device of claim 1, wherein the at least one second section forms a hinge between adjacent individual ones of the plurality of first sections.

7. The device of claim 1, wherein the plurality of first sections and the at least one second section are formed via unitary construction from the same material.

8. The device of claim 1, wherein the at least one second section is a groove between adjacent individual ones of the plurality of first sections.

9. The device of claim 1, wherein the at least one second section is thinner than the plurality of first sections.

10. The device of claim 1, further comprising a cover coupled to the flexible patch over the plurality of electrical components and support structure.

11. The device of claim 1, wherein the plurality of electrical components are adapted to process data indicative of an analyte level.

12. The device of claim 11, further comprising a sensor configured to output the data indicative of the analyte level, wherein the sensor is coupled to one or more electrical components of the plurality of electrical components.

13. The device of claim 1, wherein the plurality of first sections and the at least one second section form one or more geometric patterns.

14. The device of claim 1, wherein the plurality of first sections and the at least one second section form a single layer on the flexible patch.

15. The device of claim 1, wherein the at least one second section is more flexible than the plurality of first sections.

16. The device of claim 1, wherein the plurality of first sections are more rigid than the plurality of second sections.

* * * * *